(12) United States Patent
Dees, Jr.

(10) Patent No.: US 7,682,362 B2
(45) Date of Patent: Mar. 23, 2010

(54) LOCKABLE ORIENTATION STYLUS

(75) Inventor: Roger Ryan Dees, Jr., Senatobia, MS (US)

(73) Assignee: Smith & Nephew, Inc., Memphis, TN (US)

( * ) Notice: Subject to any disclaimer, the term of this patent is extended or adjusted under 35 U.S.C. 154(b) by 1032 days.

(21) Appl. No.: 11/344,778

(22) Filed: Feb. 1, 2006

(65) Prior Publication Data

US 2006/0179979 A1    Aug. 17, 2006

Related U.S. Application Data

(60) Provisional application No. 60/649,059, filed on Feb. 1, 2005.

(51) Int. Cl.
*A61B 17/58* (2006.01)
*A61B 1/00* (2006.01)

(52) U.S. Cl. .................. 606/86 R; 606/88; 33/512; 600/587

(58) Field of Classification Search ......... 600/587–595; 606/86 R, 87–89, 102, 130; 33/511–515; 81/9.2
See application file for complete search history.

(56) References Cited

U.S. PATENT DOCUMENTS

| | | | |
|---|---|---|---|
| 2,309,502 A * | 1/1943 | Douglas | ............... 604/135 |
| 4,393,868 A | 7/1983 | Teague | |
| 4,471,993 A | 9/1984 | Watson | |
| RE31,809 E | 1/1985 | Danieletto et al. | |
| 4,604,997 A | 8/1986 | De Bastiani et al. | |
| 4,736,742 A | 4/1988 | Alexson et al. | |
| 4,834,092 A | 5/1989 | Alexson et al. | |
| 4,887,865 A | 12/1989 | Dawidzon | |
| 4,936,843 A | 6/1990 | Sohngen | |
| 4,976,713 A | 12/1990 | Landanger et al. | |
| 5,003,965 A | 4/1991 | Talish et al. | |
| 5,035,700 A | 7/1991 | Kenna | |
| 5,049,151 A | 9/1991 | Durham et al. | |
| 5,305,203 A | 4/1994 | Raab | |
| 5,368,549 A | 11/1994 | McVicker | |
| 5,454,810 A | 10/1995 | Pohl et al. | |
| 5,456,655 A | 10/1995 | Morris | |
| 5,462,550 A | 10/1995 | Dietz et al. | |
| 5,484,446 A | 1/1996 | Burke et al. | |
| 5,549,703 A | 8/1996 | Daigle et al. | |
| 5,556,374 A | 9/1996 | Grace et al. | |
| 5,667,507 A | 9/1997 | Corin et al. | |

(Continued)

OTHER PUBLICATIONS

Femoral Anterior Stylus schematic described as 'Lock knob (threaded) which locks arm from all movement,' one page (1997).

(Continued)

*Primary Examiner*—Eduardo C Robert
*Assistant Examiner*—Julianna N Harvey
(74) *Attorney, Agent, or Firm*—Kilpatrick Stockton LLP

(57) ABSTRACT

The present invention relates generally to devices and methods for identifying landmarks on the anatomy of a human for reference in a surgical procedure. In certain embodiments of the present invention, a stylus body is provided with a spring member and stop with openings having different shaped portions so that when the stop is depressed it can free the stylus arm and allow rotation and/or translation and, when released, it can lock the stylus arm from rotating and/or translating.

9 Claims, 6 Drawing Sheets

U.S. PATENT DOCUMENTS

| | | | |
|---|---|---|---|
| 5,683,397 | A | 11/1997 | Vendrely et al. |
| 5,697,158 | A | 12/1997 | Klinzing et al. |
| 5,700,268 | A | 12/1997 | Bertin |
| 5,711,297 | A | 1/1998 | Iliff |
| 5,725,532 | A | 3/1998 | Shoemaker |
| 5,748,767 | A | 5/1998 | Raab |
| 5,827,208 | A | 10/1998 | Mason et al. |
| 5,928,234 | A | 7/1999 | Manspeizer |
| 5,980,475 | A | 11/1999 | Gibbons |
| 6,027,507 | A * | 2/2000 | Anderson et al. ........... 606/102 |
| 6,077,270 | A | 6/2000 | Katz |
| 6,139,548 | A | 10/2000 | Errico |
| 6,162,228 | A | 12/2000 | Durham |
| 6,162,234 | A | 12/2000 | Freedland et al. |
| 6,175,979 | B1 | 1/2001 | Jackson |
| 6,193,724 | B1 | 2/2001 | Chan |
| RE37,338 | E | 8/2001 | McVicker |
| 6,290,704 | B1 | 9/2001 | Burkinshaw et al. |
| 6,300,941 | B1 | 10/2001 | Segalle |
| 6,402,756 | B1 | 6/2002 | Ralph et al. |
| 6,436,058 | B1 | 8/2002 | Krahner et al. |
| 6,447,548 | B1 | 9/2002 | Ralph et al. |
| 6,532,002 | B2 | 3/2003 | Segalle |
| 6,554,864 | B2 | 4/2003 | Ralph et al. |
| 6,558,423 | B1 | 5/2003 | Michelson |
| 6,595,936 | B1 | 7/2003 | Oladipo |
| 6,595,994 | B2 | 7/2003 | Kilpela et al. |
| 6,605,092 | B2 | 8/2003 | Grumberg et al. |
| 6,666,867 | B2 | 12/2003 | Ralph et al. |
| 6,673,114 | B2 | 1/2004 | Hartdegen et al. |
| 6,689,134 | B2 | 2/2004 | Ralph et al. |
| 6,729,794 | B2 | 5/2004 | Callaway et al. |
| 6,746,453 | B2 | 6/2004 | Deloge et al. |
| 6,837,904 | B2 | 1/2005 | Ralph et al. |
| 6,890,356 | B2 | 5/2005 | Ralph et al. |
| 6,916,325 | B2 | 7/2005 | Kana et al. |
| 6,925,339 | B2 | 8/2005 | Grimm et al. |
| 6,951,561 | B2 | 10/2005 | Warren et al. |
| 6,974,483 | B2 | 12/2005 | Murray |
| 6,991,802 | B1 | 1/2006 | Ahola et al. |
| 7,001,346 | B2 | 2/2006 | White |
| 7,008,422 | B2 | 3/2006 | Foley et al. |
| 7,041,135 | B2 | 5/2006 | Michelson |
| 2002/0173797 | A1 | 11/2002 | Van Zile et al. |
| 2003/0040752 | A1* | 2/2003 | Kitchens ...................... 606/86 |
| 2003/0114859 | A1 | 6/2003 | Brusin et al. |
| 2003/0149378 | A1* | 8/2003 | Peabody et al. ............. 600/587 |
| 2003/0153924 | A1 | 8/2003 | Kana et al. |
| 2004/0039395 | A1 | 2/2004 | Coon et al. |
| 2005/0049603 | A1 | 3/2005 | Calton et al. |
| 2005/0149042 | A1 | 7/2005 | Metzger |
| 2005/0203528 | A1 | 9/2005 | Couture et al. |
| 2005/0261696 | A1 | 11/2005 | Overes et al. |
| 2005/0273115 | A1 | 12/2005 | Coon et al. |

OTHER PUBLICATIONS

Revision Tibial Stylus schematic, one page (2004).

Schematic described as 'Spring and nylon washer provide resistance to the stylus arm to provide resistance to translation, yet allows it when force is applied,' one page (2003).

Anterior Stylus Assembly schematic described as 'This stylus only allows rotation of the stylus arm around the connection axis,' one page (1996).

Brochure entitled Genesis II® Total Knee System Primary Surgical Technique by Smith & Nephew, 36 pages (1998).

* cited by examiner

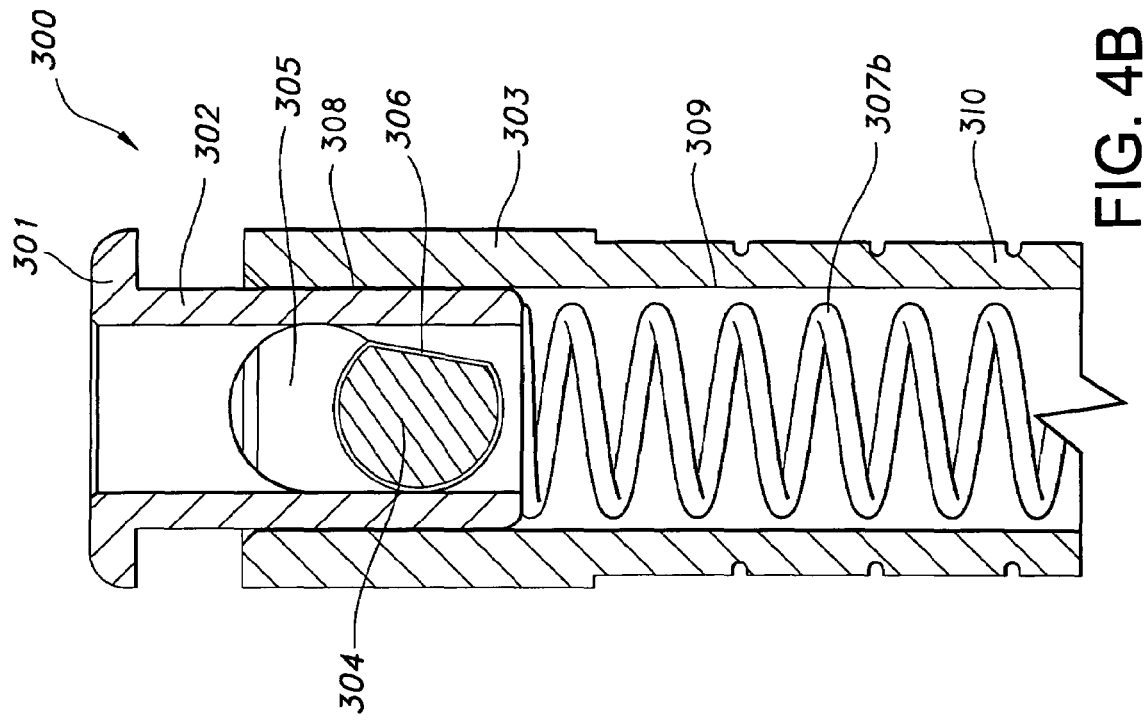
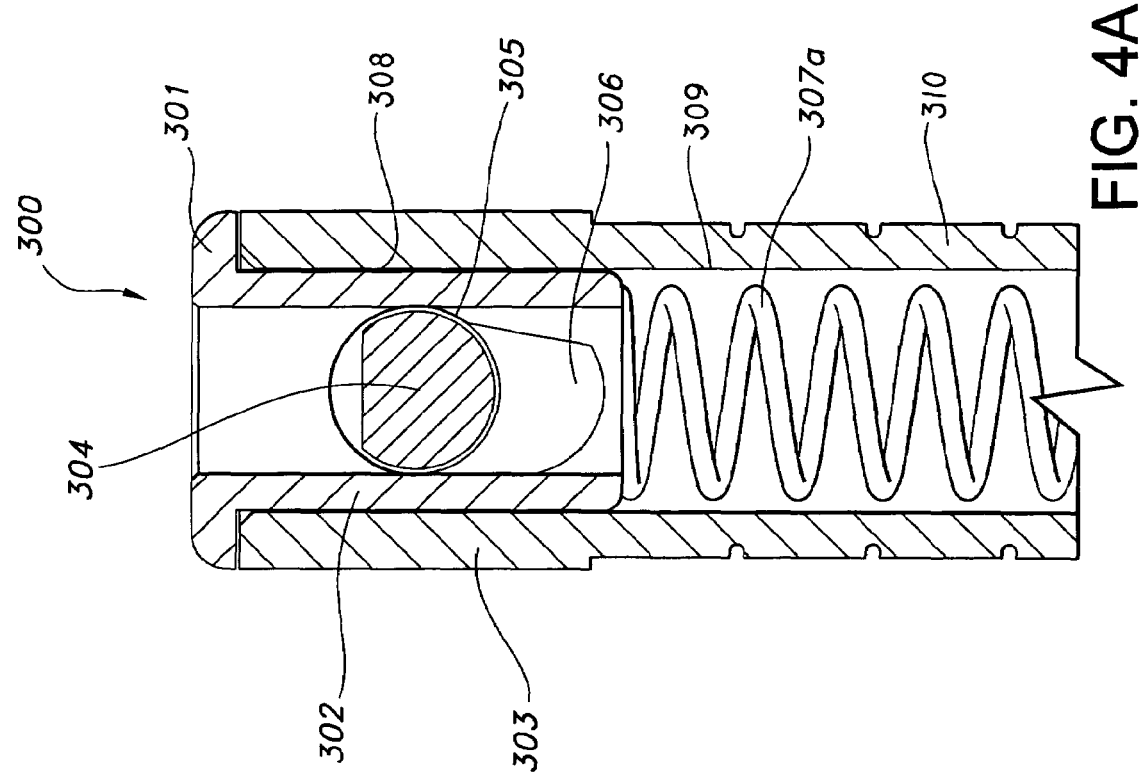

LOCKABLE ORIENTATION STYLUS

CROSS REFERENCE TO RELATED APPLICATIONS

This application claims the benefit of U.S. Provisional Application No. 60/649,059 filed Feb. 1, 2005, the contents of which are incorporated herein by reference.

TECHNICAL FIELD OF INVENTION

This invention relates to devices and methods for identifying landmarks on the anatomy of a patient for reference in a surgical procedure.

BACKGROUND OF THE INVENTION

Certain surgical procedures, such as orthopedic surgery, generally involve preparing a particular bone for attaching a sizing guide to the particular bone and resecting the particular bone in order to fit it with a prosthesis. An example of one such procedure is found in connection with the GENESIS II® Total Knee System by Smith & Nephew.

In a procedure such as the GENESIS II® Total Knee System, the surgeon first flexes the knee to 70-90° and performs a longitudinal incision over the anterior aspect of the knee along the medial border of the patella. The surgeon then retracts the patella laterally. Using a drill, a hole is made into the distal femur for an intramedullary rod. A valgus alignment guide and anterior cutting guide are connected to the intramedullary rod and inserted into the distal femur. The surgeon resects the anterior femur using the anterior cutting guide and a conventional resecting stylus guide such as that illustrated in FIG. 1. A conventional stylus 10 generally includes a stylus body 12, stylus shaft 14, stylus arm 16, an arm knob 18, and a locking mechanism such as a screw 20.

After removing the intramedullary rod, valgus alignment guide, and anterior cutting guide, the surgeon attaches a femoral sizing guide to the distal femur. The femoral sizing guide may also include a sizing guide stylus, similar to the conventional stylus 10, for example, illustrated in FIG. 1, to assist in referencing a position. The surgeon utilizes the stylus to determine the size of the prosthetic component from indicia on the stylus shaft 14. Once a reference point is found with the stylus arm 16, the surgeon turns the locking mechanism 20, which locks the stylus arm 16 into place. An appropriate reading of the stylus shaft 14 is taken, the stylus and sizing guide are removed and a prosthetic component is then attached.

As stated above, generally a stylus is utilized by the surgeon to resect a bone while referencing an unaffected area of the bone. In the particular case of knee surgery, for instance, this may include the tibial plateau or the femoral anterior. To reference an unaffected area, the surgeon manipulates the stylus height relative to the bone by moving the stylus body up or down. Furthermore, the surgeon manipulates the stylus arm by the arm knob in the rotational and translational direction to obtain an appropriate reference for resecting. Once an appropriate reference is determined, conventionally, the surgeon utilizes a screw or cam-lock means to prevent the stylus arm from rotating in the translational or rotational directions. Alternatively, a spring may be conventionally utilized to provide resistance to rotation but not prevent rotation.

Current surgical techniques attempt to reduce ancillary tissue damage performed during a surgical procedure. Such minimally invasive surgical techniques have resulted in less disturbance and potential trauma to soft tissue which would have been either removed or moved for greater access to the surgical area of the body in conventional surgery. Minimally invasive surgical techniques have, however, created issues with respect to navigating and maneuvering instruments in the presence of soft tissue. For example, in orthopedic surgery, the stylus arm must be manipulated against unaffected areas of the bone under soft tissue.

Conventional stylus locking structures generally involve either several steps to lock the stylus arm or do not completely prevent stylus arm rotation. For example, locking with a screw or cam-lock involves the surgeon applying the necessary torque to ensure that the screw or cam-lock does not loosen while a reference is made for resecting. There is a danger that the surgeon may not sufficiently tighten or lock the screw or cam-lock means and the stylus arm, unknown to the surgeon, rotates during the procedure. Additionally, even if the surgeon sufficiently tightens the screw or cam-lock, the stylus arm may still become disengaged if the screw or cam-lock is jarred, or otherwise, during the procedure. Furthermore, as stated previously, the conventional spring mechanism only provides resistance to the stylus arm rotating and does not entirely prevent rotation in either the rotational or translational directions.

During minimally invasive surgical techniques, especially, soft tissue may cause pressure to be placed on the stylus arm and cause the stylus arm to change position. The soft tissue may also cause pressure to be placed on the stylus locking mechanism and cause the locking mechanism to become unlocked, thereby possibly allowing the stylus arm to change position and, possibly, without the surgeon's knowledge. The consequences of a stylus arm unintentionally or unknowingly rotating may impair the integrity of the particular orthopedic procedure or even the health and welfare of the patient. The surgeon, for instance, may be unable to make a correct resection due to the stylus arm rotating while the surgeon is determining a reference for the resection. Furthermore, a stylus arm that unknowingly rotates may cause the surgeon to choose an incorrectly sized prosthesis and prolong the surgical procedure or adversely affect the results of the procedure.

Therefore, there is a need for a stylus that will allow a surgeon to rotate the stylus arm in the rotational and translational direction and lock the stylus arm to a particular position, when desired, while preventing the stylus arm from becoming unintentionally or accidentally unlocked. Additionally, there is a need for a stylus in which a surgeon can easily and quickly lock the stylus arm and one that provides the surgeon with an indication that the stylus arm is indeed locked. Such devices can be particularly useful in minimally invasive surgery.

SUMMARY OF THE INVENTION

Accordingly, the present invention includes new devices and methods for identifying landmarks on the anatomy of a human for reference in a surgical procedure. In some embodiments of the present invention, a stylus body is provided with openings, opposite one another, in the sides of the top of the stylus body. The stylus body may also contain a cavity or opening extending from the top of the stylus body and into the stylus body. A spring may be provided and located inside the cavity and a stop may also be provided with two openings, opposite each other on the sides of the stop. The stop openings may preferably include a first portion with a first shape and a second portion with a second shape. Additionally, the stop may be received in the cavity and partially extending out of the top of the stylus body. A stylus arm may also be provided with a portion that has a flat, and is partially received in the openings in the stylus body and the stop. The second portion of the stop opening may be configured to prevent the stylus arm from rotating when the stylus arm penetrates the second portion. The first portion of the stop opening may allow the stylus arm to rotate when the stylus arm penetrates the second portion. The stylus arm may include one end that may be used to contact an unaffected portion for referencing and another end that may include a detachable arm knob.

The stop may be depressed, compressing the spring and aligning the first portion of the stop opening with the openings in the stylus body. The stylus arm may then be rotated in the rotational and translational direction, as necessary, to maneuver the stylus arm under the soft tissue and obtain an appropriate reference point on the bone. When an appropriate reference point is determined, a first end of the stylus arm is generally pointed downward, the stop may be released and the spring causes the stop to move upward. The stylus arm then penetrates the second portion of the stop opening as the spring pushes the stop upward. The stylus arm will be preferably prevented from rotating by the particular configuration of the second portion of the stop opening and part of the stylus arm, which cooperates with each other in shape or otherwise and also, if desired, using some or all of the force imparted by the spring to stop or reduce rotation or translation.

After completing the necessary surgical procedural steps that utilize a stylus, the stop may be depressed, thereby allowing the stylus arm to penetrate the first portion of the stop opening, so that it can rotate and translate and be removed as desired.

A surgeon may utilize a stylus according to various embodiments of the present invention to perform a variety of surgical procedures, such as minimally invasive orthopedic surgical procedures, with confidence that the stylus arm will be locked into place. A stop, according to certain aspects of the present invention, may, when desired, prevent the stylus arm from rotating and/or translating even when the stylus arm is under pressure from soft tissue or other sources.

An advantage of certain aspects and embodiments of the present invention is to provide a stylus with a device to and quickly lock a stylus arm in place easily during a surgical procedure.

A further advantage of certain aspects and embodiments of the present invention is to decrease the likelihood that a stylus arm will be unintentionally or unknowingly rotated during a surgical procedure.

A still further advantage of certain aspects and embodiments of the present invention is the ability to allow rotation of the stylus arm when it is desired but lock the stylus arm in a certain position after the desired rotation is completed.

A still further advantage of certain aspects and embodiments of the present invention is the ability to prevent rotation even when soft tissue applies pressure to the stylus arm.

A still further advantage of certain aspects and embodiments of the present invention is that it allows rotation or locks the stylus into place without requiring several steps.

A still further advantage of certain aspects and embodiments of the present invention is the ability to provide an accurate reference point to a surgeon during a surgical procedure.

BRIEF DESCRIPTION OF THE DRAWINGS

FIG. 4a is a cross-sectional view of a stylus stop and a stylus arm in the rotating position according to one embodiment of the invention.

FIG. 4b is a cross-sectional view of the stylus stop and stylus arm of FIG. 4a in the non-rotating position.

DETAILED DESCRIPTION OF THE INVENTION

Figure 1:
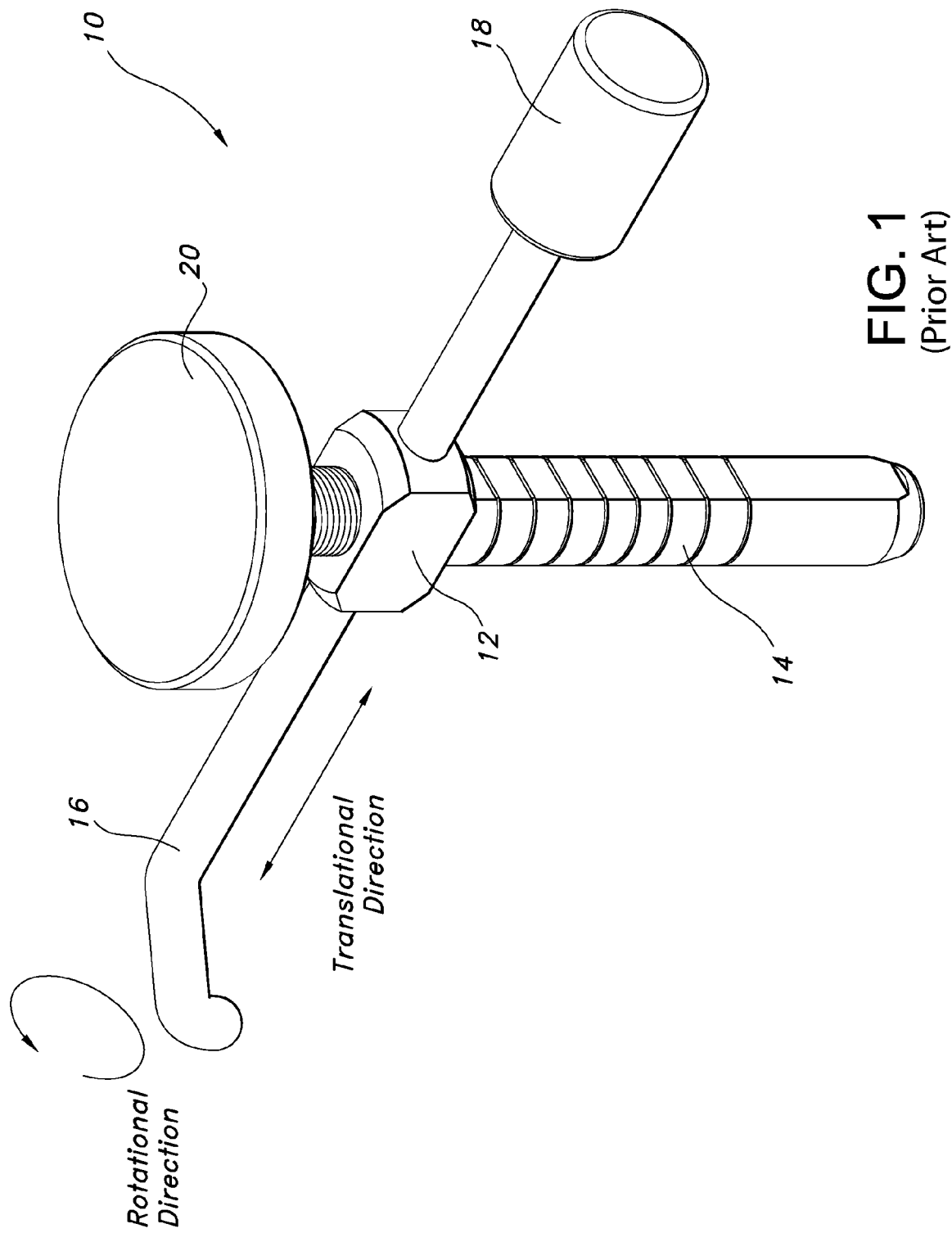
FIG. 1 is a perspective view of a conventional stylus with a screw locking mechanism.
Figure 2:
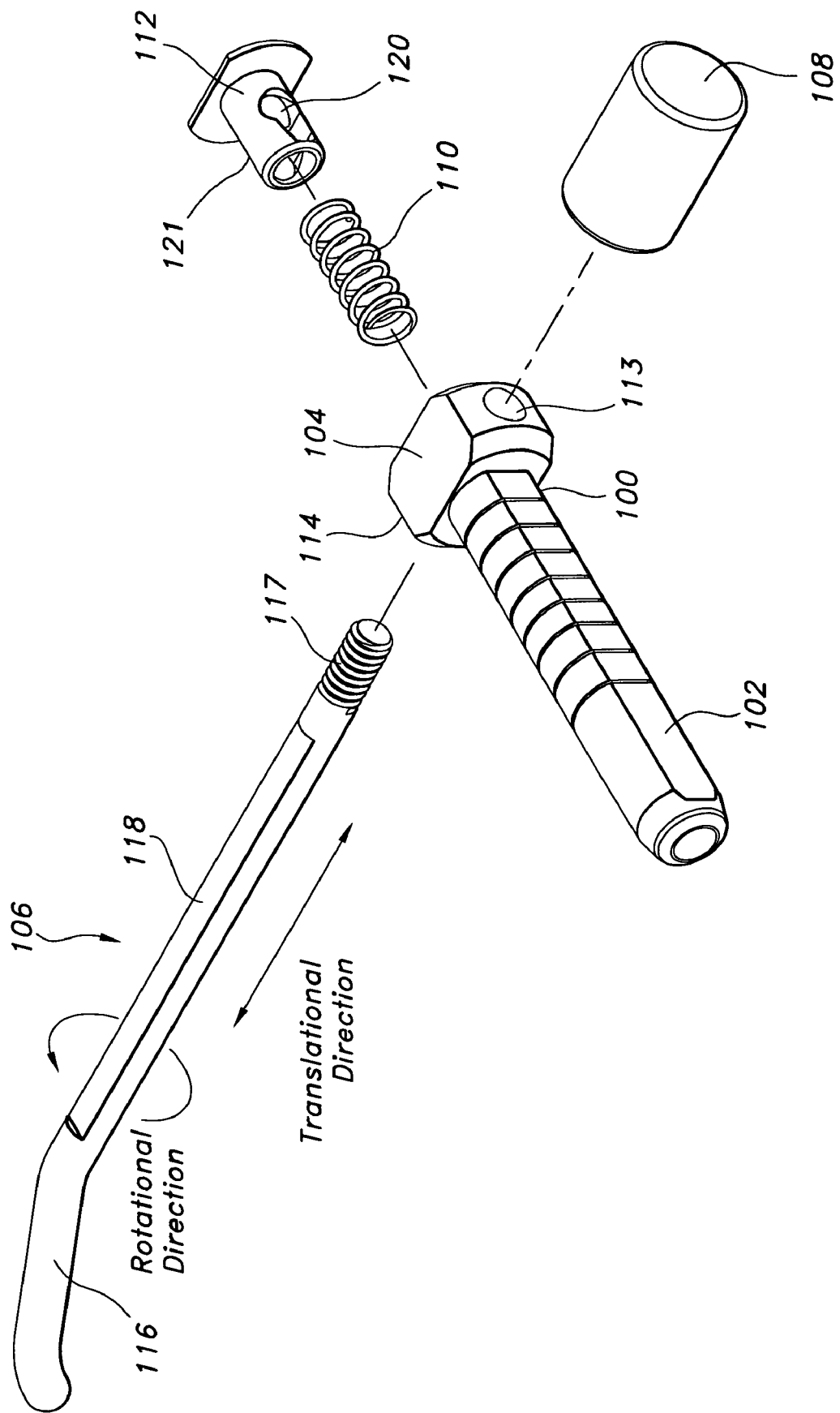
FIG. 2 is an exploded perspective view of a lockable stylus according to one embodiment of the invention.

Referring initially to FIG. 2, illustrated are parts of a stylus according to one embodiment of the present invention. Included in this particular embodiment is a stylus body 100 that includes a stylus shaft 102 and an upper member 104, stylus arm 106, an arm knob 108, a spring member 110, and a stop 112. In the particular embodiment illustrated in FIG. 2, the stylus body upper member 104 has two openings 113, 114 in two sides opposite one another for receiving a stylus arm 106. The openings 113, 114 are preferably circular in shape but may be any shape to allow rotation by the stylus arm 106. The stylus body upper portion 104 preferably also includes a cavity 308 of FIGS. 4a and 4b extending from the top of the upper member 104 to the stylus shaft 102 or as far as otherwise desired. The stylus shaft 102 is essentially an elongated member that extends from the stylus body upper member 104. The stylus shaft 102 preferably includes a cavity 308 of FIGS. 4a and 4b extending from stylus body upper member 104, which can communicate with the cavity and upper member 104, such as for receiving a spring member 110 or other component.

The stylus arm 106 is preferably a metallic member with a first end 116 that is curved downward for referencing a reference bone portion and a second end 117 that preferably includes a threaded portion for receiving and holding an arm knob 108. Alternatively, the second end 117 may include any configuration that is adapted to receive and hold the arm knob 108. The stylus arm 106 also preferably includes at least one essentially flat portion 118 ("flat") that extends, preferably, between the first end 116 and second end 117. As will be more clearly understood below, the flat portion 118 cooperates with the stop 112 to prevent or allow the stylus arm 106 to rotate or translate relative to the stylus body 100.

According to the specific embodiment illustrated in FIG. 2, the spring 110 may preferably be located within the cavity 308 and 309 of the stylus body upper member 104 and stylus shaft 102. While in the cavity 308 and 309, the spring 110 may preferably cooperate with the stop 112 to control the rotation of the stylus arm 106. The stop 112 may therefore be located in the cavity 308 of the stylus body upper member 104 for manipulation into a first position to allow rotation of the stylus arm 106 and to be locked into a second position to prevent rotation and/or translation of the stylus arm 106. The stop 112 preferably includes two openings 120, 121 opposite one another and located on the sides of the stop 112. In certain preferred embodiments of the present invention, the openings 120, 121 may include a first portion and second portion that are of different shapes. As will be more apparent below, the first portion preferably allows the stylus arm 106 to rotate while the second portion preferably prevents the stylus arm 106 from rotating.

As stated previously, the spring 110 is inserted into the cavity 308 and 309 of FIGS. 4a and 4b of the stylus shaft 102 and stylus body upper member 104. The stop 112 is preferably inserted into, at least, the cavity 308 of the stylus body upper member 104. Alternatively, the stop 112 may be inserted into the cavity 308 and 309 of the stylus body upper member 104 and at least a portion of the stylus shaft 102. The stop 112 is initially in a first position but may be depressed and held into a second position thereby compressing the spring.

Figure 3:
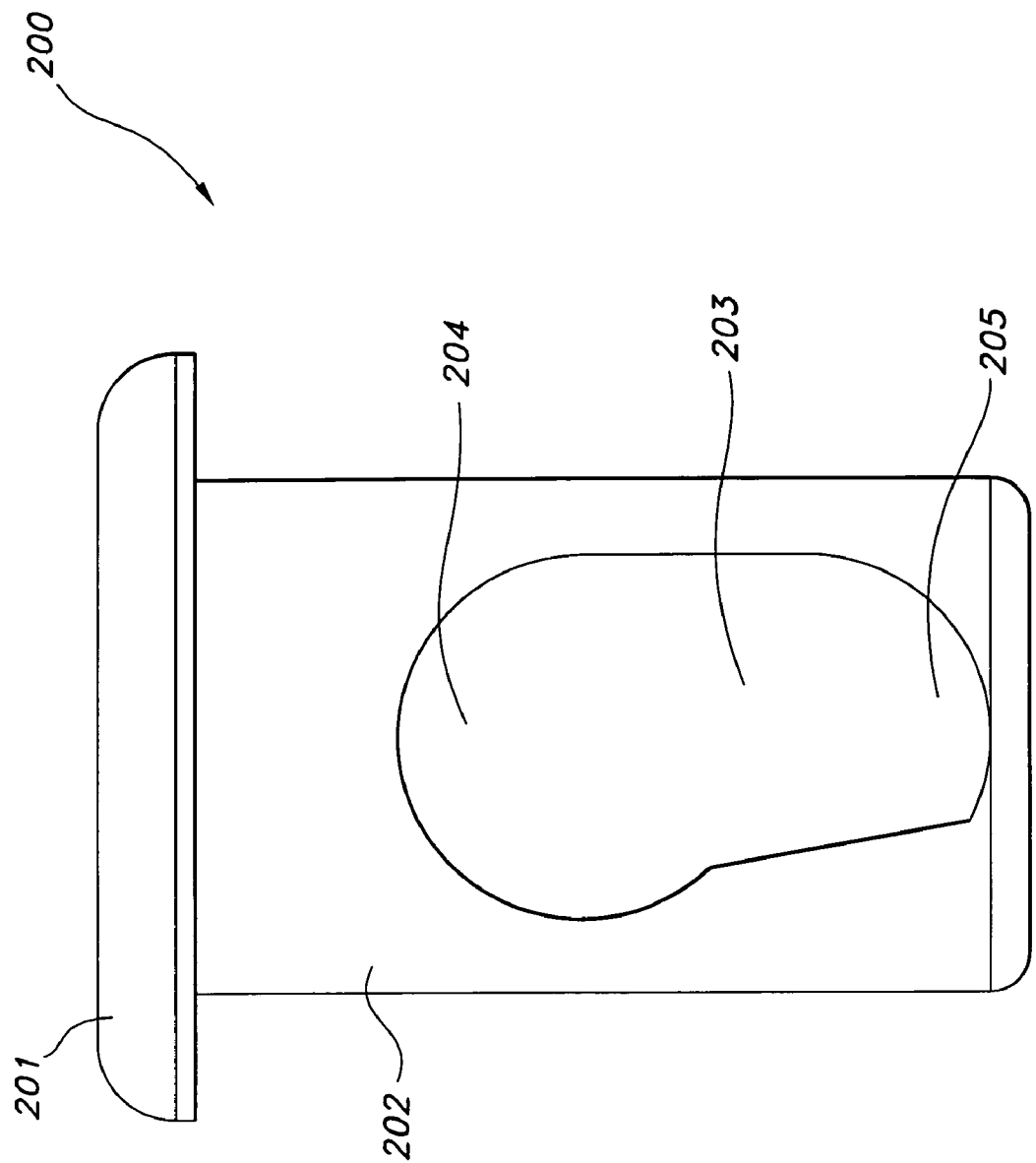
FIG. 3 is a side view of a stylus stop according to one embodiment of the invention.

Referring now to FIG. 3, illustrated is a side-view of one embodiment of a stop 200 of the present invention. The stop 200 specifically illustrated in FIG. 3 includes a button portion 201 and a stop body 202 extending from the button portion 201. The button portion 201 is preferably any rigid structure that is capable of receiving pressure, directed on top of the button portion 201. The opening 203 of the stop 200 includes a first portion 204 and a second portion 205. In certain preferred embodiments of the present invention, the first portion 204 may be essentially circular in shape while the second portion may be essentially D-shaped. In particular preferred embodiments of the present invention, the first portion 204 allows the stylus arm 106 to rotate and/or translate when the stylus arm 106 is received in or penetrates the first portion 204. The second portion 205 preferably prevents the stylus arm 106 from rotating and/or translating when the stylus arm 106 is received in the second portion 204.

Referring now the FIGS. 4a and 4b, illustrated are cross-sectional views of a stylus stop 300 and a stylus arm 304 in the non-rotating position according to one preferred embodiment of the present invention. The stylus stop 300 in FIGS. 4a and 4b includes a button portion 301 with a stop body 302 extending from the button portion 301. The stylus stop 300 in FIG. 4a is being depressed and is located in the cavity 308 of the stylus body 303 and, if desired, cavity 309 of the stylus shaft 310. In this position, the stylus stop 300 is preferably compressing a spring 307a.

The stylus stop 300 also preferably includes openings with a first portion 305 that is essentially circular in shape and a second portion 306 that is essentially D-shaped, or any other desired shape. A cross-section of a stylus arm 304 is illustrated in FIG. 4a and has a shape that cooperates with the shape of the second portion 306 of the stylus stop openings to control rotation and/or translation of the stylus arm 304. In FIG. 4a, the stylus stop 300 is being depressed and the stylus arm 304 penetrates the first portion 305 of the stylus stop opening. Since the first portion 305 is larger than the cross-sectional portion of the stylus arm 304, the stylus arm 304 may be rotated and/or translated.

FIG. 4b illustrates a stylus stop 300 that is released from the depressed position. The spring 307b is extended and pushes the stylus stop 300 upwards when the force pushing downward on the button portion 301, as in FIG. 4a, is released and the stylus arm 304 is rotated into a position in which it will fit in the second portion 306 of the stylus stop 300 opening. The upward force exerted by the spring 307b on the stylus in this embodiment positions the stop 300 so that the stop 300 preferably locks the stylus arm 304 into position to prevent rotation and/or translation by the cooperation of shapes of the arm 304 and second portion 306.

Figure 5:
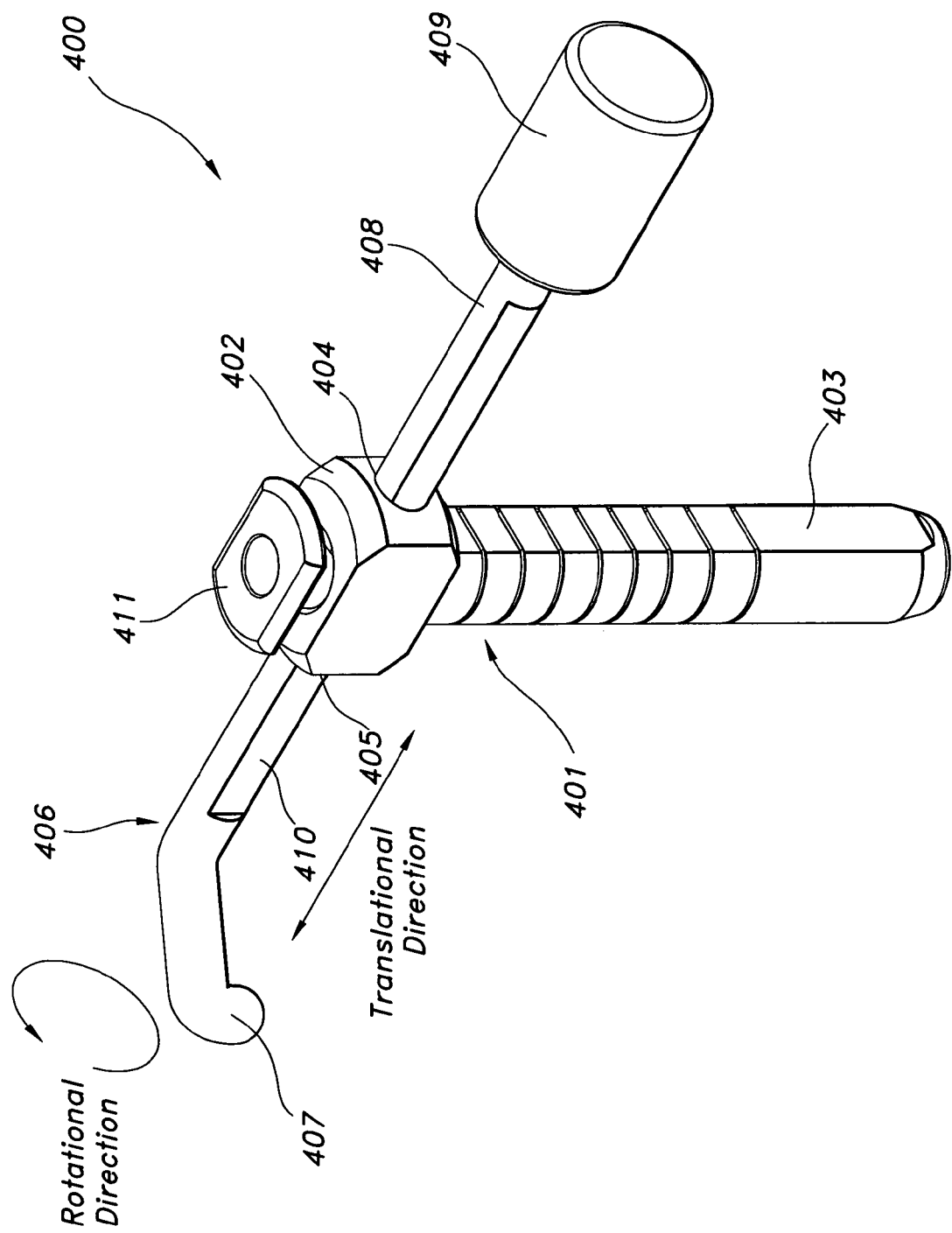
FIG. 5 is a perspective view of an assembled stylus according to one embodiment of the invention.

Referring now to FIG. 5, a preferred embodiment of the stylus of the present invention is shown. The stylus 400 includes a stylus body 401 with a stylus body upper portion 402 and a stylus shaft 403. The stylus body upper portion 402 has two openings 404, 405 opposite one another and on the sides of the stylus body upper portion 402, where a stylus arm 406 penetrates the two openings 404, 405. The stylus arm 406 of the particular embodiment illustrated in FIG. 5 includes a curved first end 407 for referencing an unaffected area of a bone and a second end 408 with an attached stylus knob 409. The stylus arm 406 preferably also includes a flat 410 that extends from the first end 407 to a second end 408. The flat portion 410 communicates with a stop 411 to prevent the stylus arm 406 from rotating and/or translating or allow the stylus arm 406 to rotate, depending on the location of the stop 411 and the forces exerted either from the button top 411 or from the spring 307a 307b, as shown in FIGS. 4a and 4b.

Preferred embodiments of the stop 411 include two openings 204 and 205 of FIG. 3 on opposing sides of the stop 411. The stop openings 204 and 205 preferably include a first portion that is essentially circular in shape and a second portion that is essentially D-shaped. The shapes of the first and second portions of the stop openings, however, may be of any shape or configuration. The stop 411 is installed in the cavity 308 of the stylus body upper portion 402 and is in communication with a spring 307a and 307b of FIGS. 4a and 4b. At least one portion of the two openings of the stop 411 are generally aligned with the two openings 404, 405 in the stylus body upper portion 402. The stop 411 may be initially in a first position, where the spring 307a, as shown in FIG. 4a, is not compressed. The stop 411, however, may be depressed into a second position, where the spring 307b, as shown in FIG. 4b, is depressed. The stop 411 stays in the second position until the force depressing the stop 411 is released.

The essentially circular stop opening is preferably aligned with the stylus body upper portion openings 404, 405 when the stop 411 is depressed and the stylus arm 406 is rotated and/or translated so that it will fit into the second preferably D-shaped portion of the stop 411 opening. When the preferably D-shaped stop opening is aligned with the stylus body upper portion openings 404, 405 the D-shaped stop opening preferably communicates with the stylus arm flat 410 to prevent the stylus arm 406 from rotating.

If the stop 411 is depressed, the spring 307b, as shown in FIG. 4b, is compressed by the stop 411. The stop 411 moves downward, preferably until the essentially circular shaped stop opening is aligned with the stylus body upper portion openings 404, 405. When the circular shaped portion is aligned with the stylus body upper portion openings 404, 405, the stylus arm 406 may be rotated and/or translated.

Although the previous descriptions of the illustrated embodiments have described the opening portions of the stop 411 as essentially "D-shaped" and "circular," it should be clear to those with skill in the art that these openings may be of any shape such that one portion allows the stylus arm to rotate and/or translate while the other portion prevents stylus arm rotation and/or translation. Furthermore, the stylus arm flat portion 410 may also be of any shape to communicate with one of the stop openings to prevent rotation.

Figure 6:
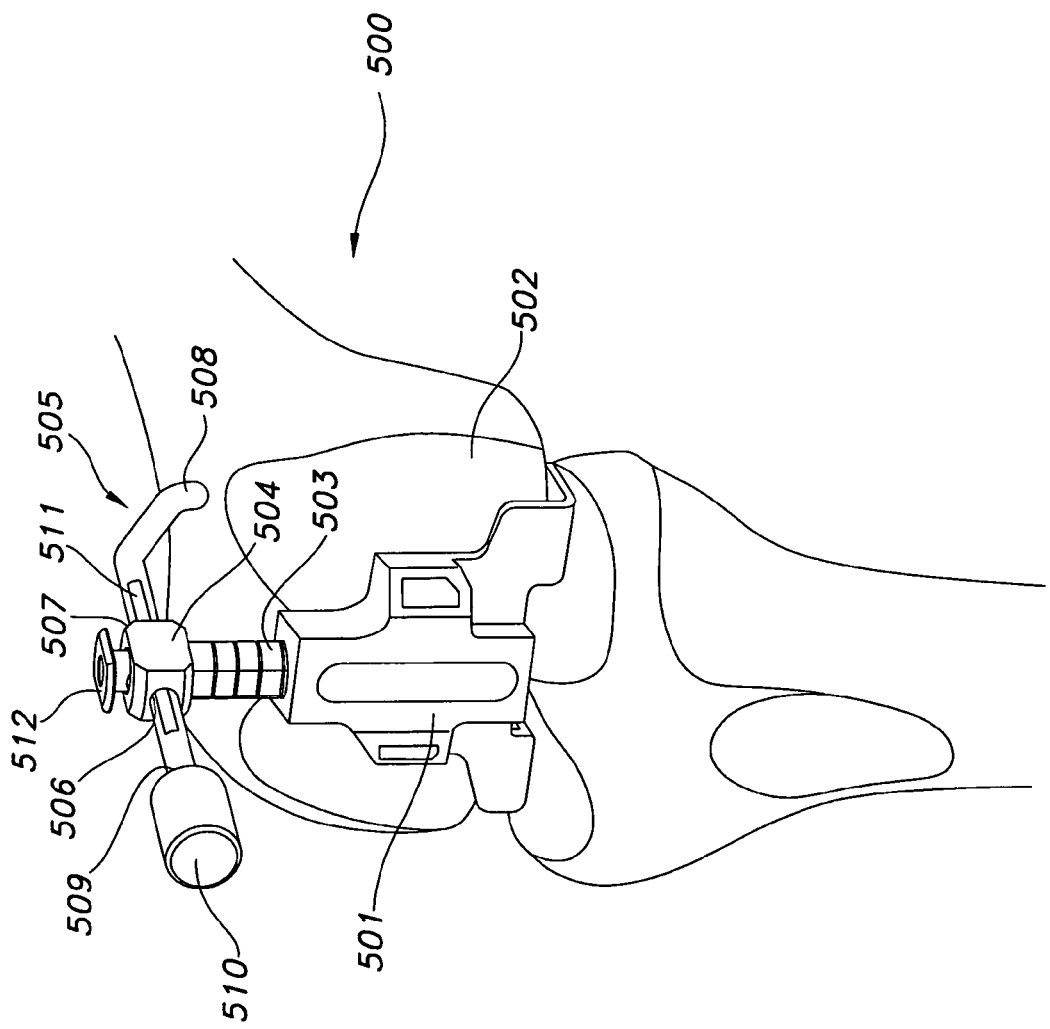
FIG. 6 shows, in perspective, a stylus referencing a reference portion during a surgical procedure according to one embodiment of the invention.

Referring now to FIG. 6, illustrated is an example of a stylus 500 according to one embodiment of the present invention being utilized during a surgical procedure on the knee. In the particular example illustrated in FIG. 6, the stylus 500 is connected with a femoral sizing guide 501 during a surgical procedure involving a knee 502. The stylus 500 includes a stylus shaft 503 and a stylus body upper portion 504 with a stylus arm 505 penetrating two opposing openings 506, 507 in the stylus body upper portion 504. The stylus arm 505 includes a slightly curved first end 508 to provide contact with the bone for reference and a second end 509 that includes an arm knob 510. The stylus arm 505 further includes a portion with a flat portion 511.

A stop 512 is illustrated without the stylus stop 512 being depressed. According to particular embodiments of the present invention, therefore, the stylus stop 512 is in a position to prevent the stylus arm 505 from rotating and/or translating. A spring 307a is located inside a cavity 309 of the stylus shaft 503 and pushes the stop 512 upward when the stop 512 is not depressed. When the stop 512 is depressed, the spring 307b is compressed and allows the stop 512 to move downward. If the stop 512 moves downward to where the circular portion of the stop 512 opening is aligned with the two opposing openings 506, 507 in the stylus body upper portion 504, the stylus arm 505 may be rotated and/or translated.

An example of a particular embodiment of the present invention, as illustrated in FIG. 6 will now be described in the particular context of a minimally invasive knee surgical procedure. After the knee 502 has been resected, a femoral sizing guide, such as, for example, the femoral sizing guide 501 in FIG. 6, is placed at the end of the resected femur. A stylus 500 is attached to the femoral sizing guide 501 by connecting the stylus shaft 503 to the top of the femoral sizing guide 501. At this point, the surgeon may depress the stop 512 and rotate and/or translate the stylus arm 505.

Specifically, the surgeon, using the arm knob 510, moves the stylus arm 505 in the translational and/or rotational direction and under soft tissue (not shown) until an appropriate reference point on the bone is located. Once the surgeon locates a desired reference point, the stop 512 may be released, the spring pushes the stop 512 upward and the stylus arm 505 preferably fits in the second portion of the stop 512 openings that are aligned with two opposing openings 506, 507 in the stylus body upper portion 504. The stylus arm 505 will then be locked into place. The surgeon may then determine the femoral prosthesis size based on the relative reference point obtained with the stylus 500, confident that the stylus arm 505 will not change position. Once the appropriate size is determined, the surgeon may depress the stop 512 until the first portion of the stop opening is aligned with two opposing openings 506, 507 in the stylus body upper portion 504 and rotate and/or translate the stylus arm 505 to remove it from under soft tissue.

The foregoing description of the embodiments, including preferred embodiments, of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the this invention.

What is claimed is:

1. A device for identifying landmarks on the anatomy of a human for reference in a surgical procedure, the device comprising:

a stylus body having an upper member with opposing first and second openings that are essentially aligned and a stylus shaft extending from the upper member, wherein the upper member and at least part of the stylus shaft comprise a cavity;

a spring member located in the cavity;

a stop partially located in the cavity and in communication with the spring member, the stop comprising a first hole opposing a second hole, the first hole and the second hole being essentially aligned, wherein each of the first hole and the second hole comprise a first shaped portion and a second shaped portion;

a stylus arm comprising
  a first end for referencing a portion of the anatomy;
  an elongated portion extending from said first end, the elongated portion having first and second shaped portions;
  a second end with a detachable knob for rotating the stylus arm; and wherein the elongated portion penetrates the first and second openings of the upper member and the first and second holes of the stop and wherein at least a portion of the first hole and at least a portion of the second hole are adapted to prevent the stylus arm from rotating or translating.

2. The device in claim 1, wherein said first shaped portion of the first hole and said first shaped portion of the second hole are circular shaped in cross-section.

3. The device in claim 1, wherein said second shaped portion of the first hole and the second shaped portion of the second hole are D-shaped in cross-section.

4. The device in claim 1, wherein the stylus arm can be rotated by depressing the stop into the cavity to allow the first shaped portion of the first hole and said first shaped portion of the second hole to be essentially aligned with the first and second openings of the upper member.

5. The device in claim 1, wherein said stylus arm first end is curved.

6. The device in claim 1, wherein said first shaped portion of the stylus arm is at least partially circular in cross-section.

7. The device in claim 1, wherein at least part of said second shaped portion of the stylus arm is a flat.

8. The device in claim 1, wherein at least part of the cross-section of the elongated portion of the stylus arm is essentially D-shaped.

9. The device in claim 1, wherein the spring member presses the stop in at least one direction to lock the stylus arm.

* * * * *